(12) United States Patent
Lenzenhuber

(10) Patent No.: US 11,759,288 B2
(45) Date of Patent: Sep. 19, 2023

(54) SYSTEM, DEVICES, AND METHOD FOR IDENTIFYING A MEDICAL TOOL

(71) Applicant: Aesculap AG, Tuttlingen (DE)

(72) Inventor: Frederick Lenzenhuber, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 133 days.

(21) Appl. No.: 17/428,046

(22) PCT Filed: Feb. 4, 2020

(86) PCT No.: PCT/EP2020/052693
§ 371 (c)(1),
(2) Date: Aug. 3, 2021

(87) PCT Pub. No.: WO2020/161111
PCT Pub. Date: Aug. 13, 2020

(65) Prior Publication Data
US 2022/0096201 A1    Mar. 31, 2022

(30) Foreign Application Priority Data

Feb. 4, 2019 (DE) ..................... 10 2019 102 685.7

(51) Int. Cl.
| | | |
|---|---|---|
| *A61B 90/98* | (2016.01) | |
| *A61B 50/20* | (2016.01) | |
| *G06K 7/10* | (2006.01) | |

(52) U.S. Cl.
CPC .............. *A61B 90/98* (2016.02); *A61B 50/20* (2016.02); *G06K 7/10366* (2013.01)

(58) Field of Classification Search
CPC ..... A61B 90/98; A61B 50/20; G06K 7/10366
(Continued)

(56) References Cited

U.S. PATENT DOCUMENTS

| 7,336,174 | B1 * | 2/2008 | Maloney | .................. | B25H 3/00 |
| | | | | | 340/568.1 |
| 2007/0023193 | A1 * | 2/2007 | King | ..................... | B25H 3/028 |
| | | | | | 166/387 |

(Continued)

FOREIGN PATENT DOCUMENTS

| CN | 108304897 A | 7/2018 |
| DE | 102015111506 A1 | 4/2016 |

(Continued)

OTHER PUBLICATIONS

Written Opinion received in International Application No. PCT/EP2020/052693 dated May 12, 2020, with translation, 15 pages.
(Continued)

*Primary Examiner* — Ahshik Kim
(74) *Attorney, Agent, or Firm* — Christopher A. Rothe; Culhane Meadows, PLLC

(57) ABSTRACT

An identification system for automatically identifying a medical tool includes at least one tool holder or packaging having a readable data carrier and designed to hold the medical tool. The system also includes an identification device to identify the medical tool. The tool holder or packaging is designed such that removal of the medical tool automatically closes a circuit provided on the tool holder or packaging and activates an antenna. The identification device is also designed to detect activation of the antenna and to read the data carrier of the tool holder or packaging.

13 Claims, 2 Drawing Sheets

(58) Field of Classification Search
USPC .......................................................... 235/451
See application file for complete search history.

(56) References Cited

U.S. PATENT DOCUMENTS

| | | |
|---|---|---|
| 2007/0115127 A1 | 5/2007 | Harper et al. |
| 2007/0152829 A1 | 7/2007 | Lindsay et al. |
| 2008/0088454 A1* | 4/2008 | Flores .................... G07G 1/009 340/572.4 |
| 2010/0252626 A1* | 10/2010 | Elizondo .............. G06Q 10/087 340/10.51 |
| 2011/0254665 A1 | 10/2011 | Lindsay et al. |
| 2016/0042130 A1* | 2/2016 | Broninx ............... G06Q 10/087 705/2 |
| 2020/0113258 A1 | 4/2020 | Guenther et al. |

FOREIGN PATENT DOCUMENTS

| | | |
|---|---|---|
| EP | 3240200 A1 | 11/2017 |
| EP | 3395291 A1 | 10/2018 |
| WO | 2018013413 A1 | 1/2018 |
| WO | 2020049044 A1 | 3/2020 |

OTHER PUBLICATIONS

Search Report received in German Application No. 10 2019 102 685.7 dated Jan. 22, 2020, with translation, 15 pages.
Search Report received in International Application No. PCT/EP2020/052693 dated May 12, 2020, with translation, 7 pages.

* cited by examiner

SYSTEM, DEVICES, AND METHOD FOR IDENTIFYING A MEDICAL TOOL

CROSS-REFERENCE TO RELATED APPLICATIONS

This application is the United States national phase entry of International Application No. PCT/EP2020/052693, filed Feb. 4, 2020, and claims the benefit of priority of German Application No. 10 2019 102 685.7, filed Feb. 4, 2019. The contents of International Application No. PCT/EP2020/052693 and German Application No. 10 2019 102 685.7 are incorporated by reference herein in their entireties.

FIELD

The present disclosure relates to an identification system for automatically identifying a medical engineering tool. In addition, the present invention relates to a tool holder, an identification device as well as a method of a corresponding identification system.

BACKGROUND

In the medical field, no automatic recognition of tools, spray cans, HF tips, ultrasonic blades, etc. is offered to date. Medical engineering tools and/or at least the packaging of the medical engineering tools are therefore usually provided with a label or marking by which one of the aforementioned application parts/handpieces, hereinafter referred to as medical tool, can be identified/recognized. At the same time, various information about the medical engineering tool to be used is of importance to an operator/user before and/or during and/or after use, for example whether and how often it has already been used, what its service life is and what its stock levels are. This kind of information is difficult or impossible to convey and maintain with the existing means.

An important aspect of medical engineering tools is the use, transmission as well as updating of tool-specific information. This may be, for example, information on whether a particular tool is suitable for a particular application and/or the condition of the particular tool, for example, in order to be able to rule out contamination of the medical engineering tool and/or to prevent injury to an operator and/or patient. Furthermore, it is crucial for the operator during the use of a medical engineering tool, in particular a motor-driven surgical tool, how the tool should and/or may be used in a particular application. This could, for example, concern the revolutions per minute of a motor-driven surgical tool.

It is prior art to mark the packaged medical engineering tools or those in a tool holder in such a way that they are recognizable to the user via labels attached to or in the packaging/tool holder. Additional information, such as maximum usability, dimensions, materials, etc., may be difficult to display on labels requiring absolute care by the supplier and may be difficult to identify by the user, for example as a result of soiling or wear.

Furthermore, in particular when handling sterile products such as surgical instruments and tools such as drills, milling cutters, etc., removal from the packaging or tool holder may be subject to restrictions, such as time pressure during a surgery. This can make it difficult for users to record and/or manually document product-specific data. Since incorrect use of medical engineering tools as a result of inadequate recording of the respective tool and its properties or use characteristics can lead to serious negative consequences, in particular for a patient, this is a problem from the prior art which is to be eliminated or at least improved by the present invention.

It is therefore not possible for the customer/operator, preferably the clinic staff, to identify which medical engineering tool is/will be inserted in an application part/handpiece without inspecting its label or outer packaging. Therefore, it is not possible to determine which product stocks are still in the warehouse (or consignment warehouse) without taking inventory. Consequently, it is also not possible for the supplier to determine which products have been combined and/or used. Overloads of medical engineering tools and the product damage that may be associated with them can only be traced with difficulty or not at all. Furthermore, no customized logistics tailored to the customer can be offered by the supplier. Displaying the possible uses of the individual medical engineering tools is also difficult.

SUMMARY

The present invention is therefore based on the object of providing an identification system for automatically identifying a medical engineering tool which avoids or at least reduces the disadvantages of the prior art.

The core of the present invention is to provide an identification device which allows identifying medical engineering tools automatically, autonomously and obligatorily, i.e. without the user having to perform or initiate this identification consciously, e.g. without the user having to look at a label. In other words, the identification device automatically recognizes, in particular during the removal process from a packaging or holder, which medical engineering tool/s is/are in use.

The object of the invention is solved by an identification system for automatic identification of a medical engineering tool, comprising at least one tool holder and/or possibly additional packaging/(outer)packaging, which is provided with a readable data carrier and which is configured to hold the medical engineering tool, and an identification device, in particular in the form of a reading device, which is configured to read out tool data from the data carrier in order to identify the medical engineering tool. The tool holder or packaging is configured in such a way that the readability of the data carrier is automatically activated by removal of the medical engineering tool, in particular an electric circuit provided on the tool holder or packaging is closed and an antenna is thereby activated, wherein the identification device is further configured to detect the activation of the readability, in particular of the antenna, and to automatically read out the data carrier of the tool holder or packaging.

For example, the identification device can be provided for an electromotively-operated surgical instrument for automatically identifying a medical engineering tool with an application part formed separately from it, which is designed to receive the medical engineering tool and in which a motor, preferably an electric motor, is integrated. Furthermore, the identification device can be configured with at least one separately formed tool holder, which is provided with a readable data carrier/data memory and in which the medical engineering tool is held and which outputs a signal when a medical engineering tool is released, preferably closes an electric circuit and thereby activates a receiver antenna. In addition, the identification device may have a separately formed instrument-actuation unit, which is preferably formed as a foot-operated control. Furthermore, the identification device may be provided with a separately formed control and/or monitoring device, which is formed as a separate device from the application part and which is preferably configured to be connected to the application part via a first cable and/or to the instrument-actuation unit via a second cable.

The tool holder serves to hold a medical engineering tool and in particular offers the advantage of making it easier for the operator to pick up the preferably sterile medical engineering tool with the application part/handpiece.

The antenna/receiver antenna and/or the electric circuit may be part of the tool holder and/or of the outer packaging of the tool holder. The electric circuit is configured in such a way that it is open, i.e. deactivated, when the medical engineering tool is arranged in the tool holder or packaging in the intended manner, and it is closed, i.e. activated, when the medical engineering tool is removed from its intended position. This has the advantage that the data carrier is not read out before the medical engineering tool is removed from the packaging, so that unnecessary data traffic and energy consumption can be prevented or reduced.

Here, the identification device may preferably be configured as an interface for communication with a control and/or monitoring device and/or with the instrument-actuation unit and/or with the tool holder as well as for transmitting and/or receiving and/or storing data and/or operating parameters. In other words, the identification system can further comprise the control and/or monitoring device in addition to the tool holder and the identification device.

In other words, this means that the identification device interacts with the tool holder and, if applicable, with at least one control and/or monitoring device/control device and/or at least one instrument-actuation unit and/or at least one application part/handpiece as well as with at least one medical engineering tool or with its tool holder, in order to transmit, store, update and/or make available, as required, the information/data that is important for the user before, during and/or after use.

A medical engineering tool in the sense of the invention is understood to mean in particular a surgical tool or operating tool with a generally distal, sharp-edged operative portion for performing an operative function and a proximal coupling portion for coupling the tool to a handle unit, in particular a drive handle unit, hereinafter referred to as handle or application part. Examples of such medical engineering instruments are, in particular, rotating tools as well as sawing tools, inter alia, drills, milling cutters, saws, screwing adapters, cutting blades or grinding adapters, which are coupled to a handle unit and/or drive unit in a generally known manner. Furthermore, the term tool in the sense of the invention is understood to mean a spray can, an HF tip, an ultrasonic blade, etc. Also, the term medical engineering tools in the sense of the invention is understood to mean implants of any type and shape, such as bone and joint implants or partial implants, stents, etc.

It is preferred if the identification device with an IC (integrated circuit or integrated circuitry) is configured to function as a reading unit and/or router and/or data server and/or server and/or repeater and/or data transmission unit.

An IC is understood to be an integrated circuitry or an integrated circuit, which is an electronic circuit mounted on a thin wafer of semiconductor material that is usually a few millimeters in size. Such electronic circuits preferably contain active and passive components in order to provide complex circuits such as microprocessors and memory chips.

In other words, the identification device in combination with the IC therein, preferably according to a chip, is a communication interface which is provided for several or at least one function(s) of the aforementioned functions. Thus, the identification device in combination with the IC is configured to serve as a reading unit, for example in order to read out the data carrier/data memory attached to/housed in the tool holder.

Furthermore, the identification device in combination with the IC has the function of a router or network router, whereby the identification device is able to move network packets or it can serve as an internet connection to couple individual, preferably local devices preferably directly. Different network technologies such as Ethernet, DSL, or BLUETOOTH® brand technology can be used for this purpose. Another advantage when the identification device acts as a router is that it can have firewall functions for the security of the system.

Furthermore, the identification device in combination with the IC with the function as data server and/or server has the advantage that a (computer) program can be included in the identification device, which as software is a program that communicates in the client-server model with another program, the client, in order to be able to use functionalities provided by the server software, such as data programs or access to a file system or a database.

Furthermore, the integration device with the IC can serve as a repeater. This is to be understood as a signal amplifier and/or signal conditioner for increasing the range of a signal. This has the advantage that the repeater can be located at a distance from the transmitting and/or receiving units and can still receive signals and forward them in conditioned form.

The identification device acts as a repeater and reading unit in order to detect activation of tool holders and preferably to collect and forward this information. Thus, the transmission and reception range of the system can be reduced.

It is preferred if the data carrier and, if applicable, the antenna, which is mounted/housed on or in the tool holder, is a readable data memory, in particular an RFID tag or an NFC tag or a BLUETOOTH® brand low energy (BLE) tag. In other words, this means that any chip technology is applicable that is able to communicate with the data carrier or data memory, in particular that is able to read it out. It is thus advantageous that the identification device can read out the data memory in order to automatically recognize the medical engineering tool when the user removes it from the packaging, preferably from the tool holder. For this, the data carrier is preferably configured for wireless communication with the identification device, and the identification device is able to detect and/or read out and/or process the data contained on the data carrier, since the application part can then be identified automatically when it is connected to the medical engineering tool.

The data written on the data carrier may be, in the sense of the invention, an article number, a lot number, a batch number, a best before date, an expiration date or a maximum use date, material, dimensions and geometries, intended use, previous uses and duration of use, and stock levels, etc.

The general idea underlying the invention therefore includes that a tool recognition/identification takes place via a separate identification device and is forwarded by data transmission to peripheral devices, such as the control and/or monitoring unit, and selected data/information and/or operating parameters are made available to the end customer/user, preferably automatically.

If the data carrier is configured as an RFID tag or NFC tag, this has the advantage in particular that data contained on it can be read out, written and processed contactlessly and automatically, in particular at any time, without requiring any special interaction on the part of the operator/user. Furthermore, it is advantageous if the data carrier can be permanently read out by the identification device.

It is preferred if the data carrier is attached to the tool holder, but attachment to an outer packaging (e.g. blister pack in which the tool may be packaged together with the tool holder) is also conceivable, wherein the data carrier can in particular be glued, molded or pressed on. As a result, accidental detachment of the data carrier or unintentional separation of the data carrier from its place of attachment is excluded, so that it can be guaranteed with a high degree of certainty that the data on the data carrier really belong to the corresponding medical engineering tool. This advantageously increases patient safety.

It is preferred if the identification device is in contact with the control and/or monitoring device via a wired or wireless communication connection. Alternatively, the control and/or monitoring device may also be another, preferably central system unit.

Furthermore, it is preferred that the wireless communication connection is preferably a WIFI® brand connection, a BLUETOOTH® brand connection, an NFC connection or a direct internet connection.

Preferably, the identification device or the control and/or monitoring device compares the tool data of one or more tools removed from the respective tool holder which were determined/received by the identification device with a stored and set application and preferably outputs a warning if the tool or at least one of the tools is not suitable for the application.

Furthermore, it is advantageous if the control and/or monitoring device automatically updates an inventory and/or treatment data set based on the tool data received from the identification device, and/or updates the tool data stored on the data carrier of the tool holder.

It is preferred if the identification device is configured to define the center of a radio range, preferably on an instrument table. In other words, it is preferred that the identification device is located in close proximity to, and ideally on, the instrument table where tool identification also takes place. In other words, the identification device provides the possibility to keep the center of the radio range variable/flexible and preferably to be established on the instrument table/instrumented table.

Therefore, it is further preferred if the identification device as an additional terminal device can decrease/reduce the radio range of the attached receiver devices in the control and/or monitoring device and/or the instrument-actuation unit, which is preferably designed as a foot-operated control. This can apply to both the transmitting and the receiving range.

It is preferred if the identification device is provided in a sterile bag to exclude contamination of medical engineering tools arranged on the instrument table or around the identification device as well as contamination of the identification device. This further increases patient safety and makes it possible to place the identification device in a sterile area.

Furthermore, it is preferred if the identification device comprises an integrated current supply/power supply. Furthermore, the control and/or monitoring device may be configured to display information received from the identification device. Furthermore, it is preferred if a separate power supply is provided, for example a mains socket, for connecting and powering the control and/or monitoring device.

Furthermore, the object underlying the invention is solved by a tool holder or packaging as well as by an identification device according to the preceding description. In particular, it is provided that the tool holder has a preferably lever-shaped or leaf spring-shaped connector, which is configured to be repositioned by removal of a tool held in the tool holder in such a way that an electric circuit is closed by the connector and an antenna is activated.

Furthermore, the present invention relates to a method for automatically identifying a medical engineering tool (if applicable for an electromotively-operated surgical instrument) via an identification system according to one of the preceding aspects.

According to the method, an identification device of the identification system can detect/identify in a first step when a medical engineering tool is removed from the tool holder. This is preferably realized by activating a (receiving and/or transmitting) antenna, which preferably sends a corresponding signal to the identification device, when the medical engineering tool is removed.

In a second step, the identification device enables identification of which medical engineering tool has been removed from the tool holder. This is realized by reading out tool data from a data carrier which is arranged on the tool holder or packaging. In a third step, the tool data are stored.

Alternatively or additionally, the tool data/information is transmitted in a fourth step to a control and/or monitoring device, which is preferably also part of the identification system. In other words, in the preferred fourth step, the identification device collects information and forwards it to the control and/or monitoring device. In a fifth step, the control and/or monitoring device optionally presents the information received from the identification device in a usable/readable manner to the user/operator. Preferably, the information is provided via a display integrated in the control and/or monitoring device. Alternatively, a display of another terminal device, such as a tablet or smartphone, can be used.

In a further preferred step, the data and/or information and/or operating parameters are updated via the identification device and the data carrier is written accordingly. Alternatively or additionally, data from the control and/or monitoring device, such as inventory or treatment statistics or patient-specific treatment data (collectively referred to as additional data), is updated.

It is preferred if the medical engineering tool removed from the tool holder is identified by reading out the data carrier, which is preferably attached to the tool holder.

It is preferred if the information and/or data and/or operating parameters stored on the data carrier can be read out and/or used for identifying whether the medical engineering tool removed from the tool holder is suitable for the intended (i.e., stored and set) application.

It is a particular advantage of the invention that, in the context of using a specific medical engineering tool, a user can safely, easily, quickly and in particular automatically obtain information about which tool he is currently using or intends to use and/or is/will be plugged into an application part, without having to look at a label or the outer packaging. In particular, an operator can automatically and easily identify whether the product being used is suitable or unsuitable for a particular application. Another advantage of the invention is that an operator can easily determine which stocks of the tool in question are still in his warehouse (or consignment warehouse) without having to take inventory. Furthermore, the identification device as an additional terminal device offers the advantage that it can be equipped with several functions and that these can be extended as required.

Furthermore, the identification device can provide protection for data and information.

In summary, it can be said that the present invention enables recognition, in particular automatic recognition/identification, via such an identification device of the respective product used, in particular of the respective tool placed on a handle/application part. Furthermore, the invention enables a particularly simple and largely error-proof maintenance and/or transmission of any product-related data written on the data carrier. In particular, the invention enables the following advantages:
- direct, automated tool recognition for the user/operator as well as for the provider (supply chain management (SCM), service, failure analysis)
- transmission of any amount of data to the user/operator as well as to the supplier (SCM, service, failure analysis)
- for the user/operator, the present invention creates a possibility to record product-related data automatically and in real time in a patient file
- long radio distances are not necessary, but are limited to the area of the instrument table.

Thus, the present invention offers significant advantages not only for the user/operator, but also for the supplier of medical engineering products and tools: with the invention, he is able to determine particularly easily which products/tools have been combined and/or used. In addition, the supplier can track overloading of tools and any associated product damage. Finally, the present invention makes it possible for a supplier to offer a customer, so to speak, tailored logistics.

BRIEF DESCRIPTION OF THE DRAWING FIGURES

DETAILED DESCRIPTION

Preferred embodiments of the present disclosure are described in more detail below based on the accompanying figures. The figures are merely schematic in nature and serve to help understanding the invention. The same elements are designated by the same reference signs.

Figure 1:
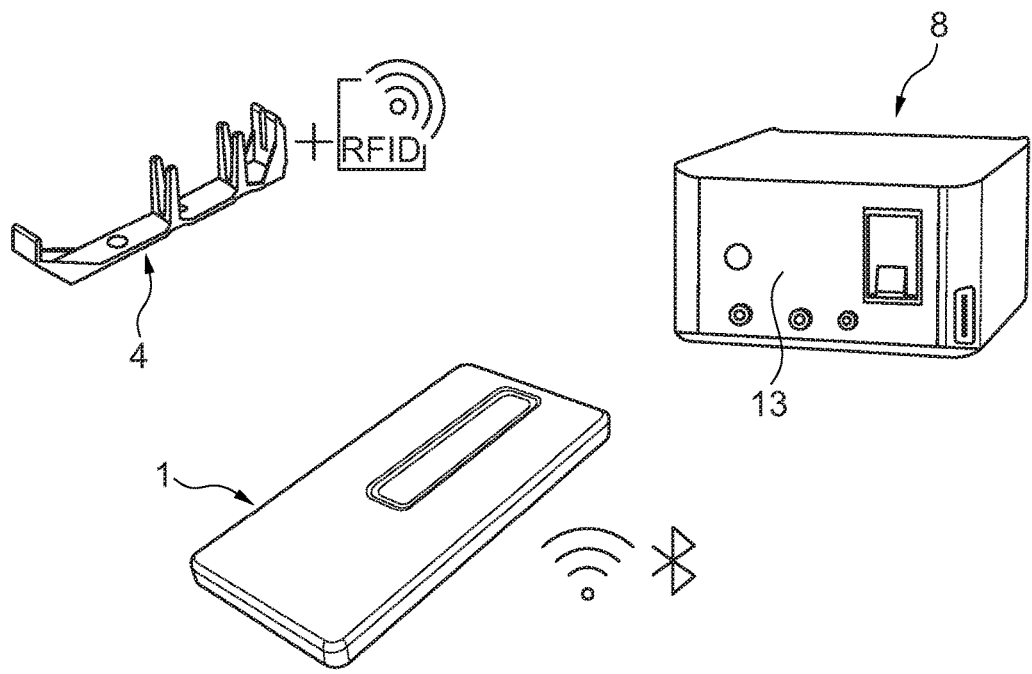
FIG. 1 is a configuration in which the identification device is shown as a reading unit for at least one tool holder according to a first embodiment.

FIG. 1 is a configuration in which the identification device 1 is shown as a reading unit for at least one tool holder 4 according to a first embodiment.

Figure 2:
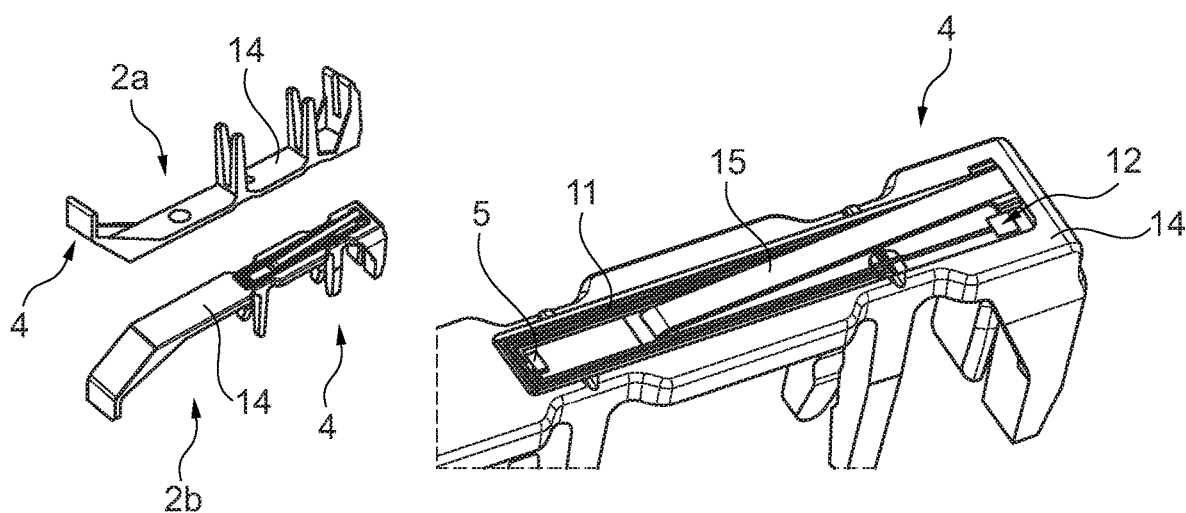
FIG. 2 is an illustration of the tool holder and its function.
Figure 3:
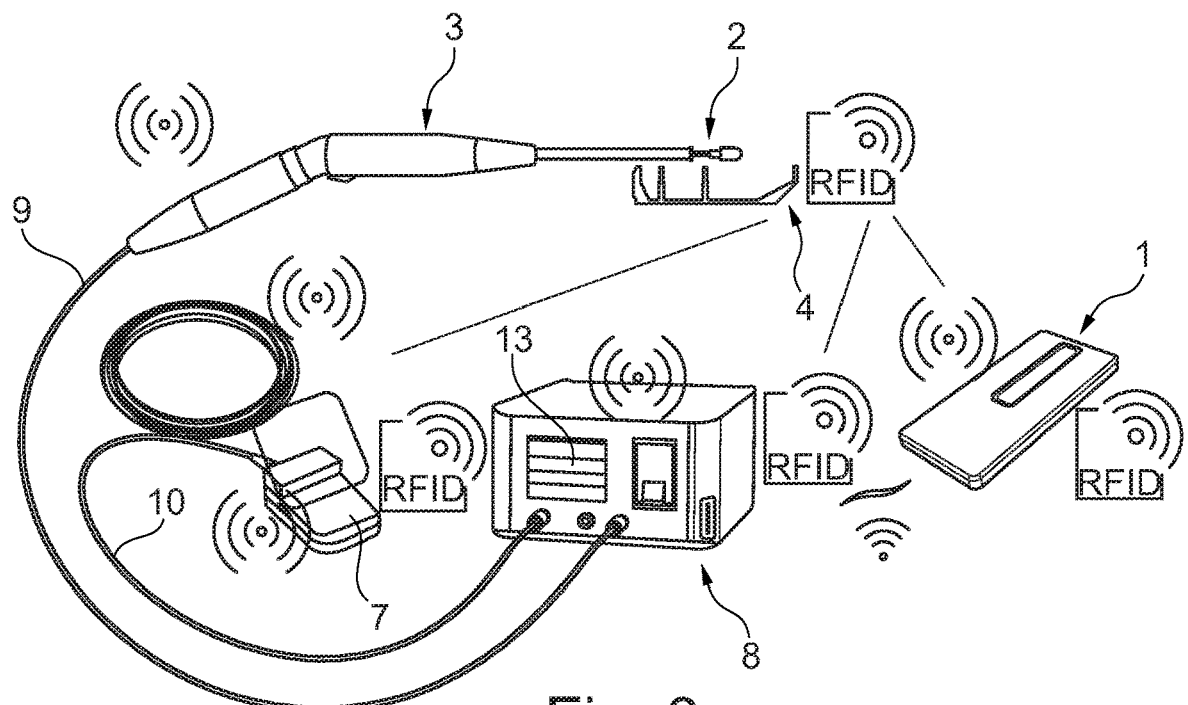
FIG. 3 is a configuration in which the identification device is shown as a repeater, server and transmission unit for at least one tool holder according to a second embodiment.

FIG. 1 shows an identification system with an identification device 1 for an electromotively-operated surgical instrument, in this case a medical engineering tool 2 (see FIG. 3). Furthermore, FIG. 1 shows a tool holder 4 formed separately from the identification device 1. The tool holder 4 receives the medical engineering tool 2. The medical engineering tool 2 can be removed from the tool holder 4 via an application part 3 (see FIG. 3). The tool holder 4 is described in detail in FIG. 2.

Separate to the identification device 1 and the tool holder 4, FIG. 1 shows a control and/or monitoring device 8, which is also formed separately from the application part 3 and is preferably connected via a first and a second cable 9 and 10 to a respective terminal device, preferably the application part 3 and an instrument-actuation unit 7 (see FIG. 3).

FIG. 1 also shows that the tool holder 4 is provided with a readable data memory, which according to the present invention is a data carrier 5 (shown in FIG. 2). Furthermore, FIG. 1 shows that according to the first embodiment, a wireless communication connection is provided via WIFI® brand technology and/or BLUETOOTH® brand technology.

The control and/or monitoring device 8 shown in FIG. 1 illustrates a display 13 that shows the information/data/operating parameters from the data carrier 5 mounted on the tool holder 4 via the data contained in the identification device 1. According to the first embodiment, the identification device 1 is designed as a reading unit that can read out the data carrier 5 and thus serves as a communication interface.

FIG. 2 is an illustration of the tool holder 4 and its function. FIG. 2 shows the tool holder 4 both in a top view 2a as well as in a bottom view 2b, wherein the bottom view is shown enlarged next to it. Only the enlarged view is described below. The tool holder 4 is configured as a molded plastic part and consists entirely of a resorbable material and has a base plate 14.

The data carrier 5 is mounted on the base plate 14. The data carrier 5 is connected to an electric circuit/aerial circuit 11 via two contacts. If the medical engineering tool 2 is housed in the tool holder 4, the electric circuit 11 is open and the receiver antenna 12 does not transmit a signal, i.e. it remains deactivated. As soon as the medical engineering tool 2 is removed from the tool holder 4, the electric circuit 11 closes via the connector 15 and activates the receiver antenna 12.

Likewise, the closing of the electric circuit can be accomplished by other constructive designs, for example by leaf springs, etc. The electric circuit 11 with the data carrier 5 can also be arranged on the underside as shown in FIG. 2 or on the top side (not shown).

FIG. 3 is a configuration in which the identification device 1 is shown as a repeater, server and transmission unit for at least one tool holder 4 according to a second embodiment.

In FIG. 3, the identification device 1 according to FIG. 1 is shown, with the difference that the identification device 1 according to the second embodiment is used both as a repeater, server and data transmission unit. Furthermore, FIG. 3 shows a tool holder 4 formed separately from the identification device 1. The tool holder 4 receives the medical engineering tool 2. The medical engineering tool 2 can be removed from the tool holder 4 via an application part 3.

Separate from the identification device 1 and the tool holder 4, FIG. 3 shows a control and/or monitoring device 8 according to FIG. 1, which is also formed separately from the application part 3 and is preferably connected to the application part 3 via a first cable 9 and to the instrument-actuation unit 7 via a second cable 10.

It can also be seen in FIG. 3 that both the tool holder 4 as well as the instrument-actuation unit 7 and the control and/or monitoring device 8 can communicate with the identification device 1 via RFID. Furthermore, FIG. 3 shows that the identification device 1 is connected to the control and/or monitoring device 8 via a WIFI® brand connection.

Thus, the configurations shown in FIGS. 1 and 3 can detect when a tool holder 4 is removed from the medical engineering tool 2 and collect the information and provide it to the system-controlling component, such as the control and/or monitoring device 8.

Figure 4:
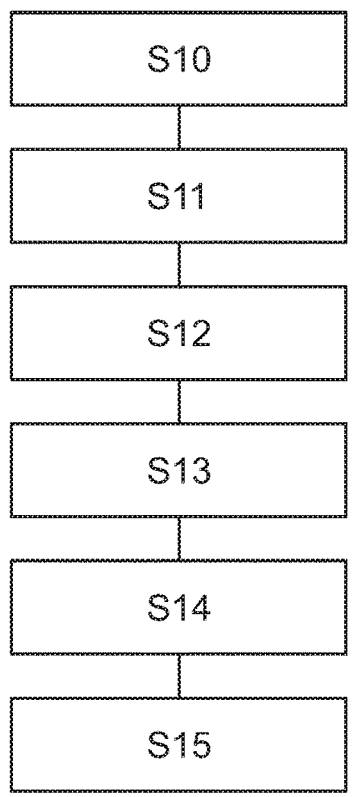
FIG. 4 is a flow chart according to the method.

FIG. 4 is a flow chart according to the present method. Accordingly, in step S10, the identification device 1 identifies whether a medical engineering tool 2 has been removed from the tool holder 4 for being received in/on an application part 3. The step S10 is based on the fact that the medical engineering tool 2 removed from the tool holder 4 activates a receiver antenna 12 by closing an electric circuit. Finally, a signal is transmitted via the activated receiver antenna 12 to the identification device 1, which thereby detects that the medical engineering tool 2 has been removed from the tool holder 4.

In a further step S11, the identification device 1 identifies which medical engineering tool 2 has been removed from the tool holder 4. Step S11 is carried out in such a way that by activating the receiver antenna 12 when the medical engineering tool 2 is removed from the tool holder 4, the identification device 1 reads out the data carrier 5 located on the tool holder 4 and thereby identifies the corresponding medical engineering tool. In a step S12, the data is stored or transmitted.

For a transmission, the identification device 1 collects information and forwards it, e.g., to the control and/or monitoring device 8. This is done either via a wireless communication connection, preferably WIFI® brand technology or BLUETOOTH® brand technology, or via a direct connection, preferably via a first cable 9. A direct internet connection is also possible.

In a further step S13, the identification device 1 detects whether the removed medical engineering tool 2 is suitable for the intended application. Step S13 is carried out in such a way that the identification device 1 can detect whether the removed tool 2 meets the requirements of the intended application based on the information, data and/or operating parameters that are stored on the data carrier 5 and that have already been read out.

In a further step S14, the control and/or monitoring device 8 presents the data/operating parameters/information transmitted/transferred by the identification device 1 on a display 13.

In a further step S15, the data/operating parameters/information are updated via and by the identification device 1 and the data carrier 5 is written accordingly. As soon as the operator returns the medical engineering tool 2 to the tool holder 5, the electric circuit is opened and the signal from the receiver antenna 12 and the reading of the data carrier 5 and the transmission of information/data/operating parameters is completed. The operator can then repeat the process or move on to another medical engineering tool 2.

The invention claimed is:

1. An identification system for automatic identification of a medical engineering tool, the identification system comprising:
   at least one tool holder and/or packaging provided with a readable data carrier and which is configured to hold the medical engineering tool; and
   an identification device configured to read out tool data from the data carrier to identify the medical engineering tool,
   the at least one tool holder and/or packaging comprising a connector configured to be repositioned by removal of the medical engineering tool,
   the at least one tool holder and/or packaging configured in such a way that readability of the data carrier is automatically activated by removal of the medical engineering tool, in such a way that an electric circuit is closed by the connector and an antenna is activated, the identification device being further configured to detect activation of the readability and automatically read out the tool data from the data carrier.

2. The identification system according to claim 1, wherein the identification device comprises an integrated circuitry and functions as at least one of a reading unit, a router, a data server, a server, a repeater and a data transmission unit.

3. The identification system according to claim 1, wherein the data carrier is configured as a readable data memory.

4. The identification system according to claim 1, wherein the identification device is in contact with a control and/or monitoring device via a wired or wireless communication connection.

5. The identification system according to claim 4, wherein the identification device or the control and/or monitoring device compares tool data of one or more tools removed from the at least one tool holder and/or packaging which were determined or received by the identification device with a stored and set application.

6. The identification system according to claim 4, wherein the control and/or monitoring device is configured to at least one of:
   automatically update an inventory and/or treatment data set based on tool data received from the identification device; and
   update the tool data stored on the data carrier of the tool holder.

7. The identification system according to claim 1, wherein the identification device is configured to define a center of a radio range.

8. The identification system according to claim 1, wherein the identification device comprises an integrated current supply.

9. A tool holder for use in an identification system having an identification device for automatic identification of a medical engineering tool,
   the tool holder comprising a readable data carrier and being configured to hold the medical engineering tool,
   the identification device configured to read out tool data from the readable data carrier to identify the medical engineering tool,
   the medical engineering tool and/or the tool holder configured in such a way that readability of the readable data carrier is automatically activated by removal of the medical engineering tool from the tool holder,
   the identification device being further configured to detect when readability of the readable data carrier is activated and automatically read out the tool data from the readable data carrier, and
   the tool holder comprising a connector configured to be repositioned by removal of said medical engineering tool when said medical engineering tool is held in the tool holder, the connector being repositioned in such a way that an electric circuit is closed by the connector and an antenna is activated.

10. An identification device for use in an identification system for automatic identification of a medical engineering tool and having at least one tool holder and/or packaging provided with a readable data carrier and configured to hold the medical engineering tool, the medical engineering tool, the at least one tool holder and/or the packaging configured in such a way that readability of the readable data carrier is automatically activated by removal of the medical engineering tool,
   the identification device being configured to read out tool data from the readable data carrier to identify the medical engineering tool, the identification device further configured to detect when readability of the readable data carrier is activated and automatically read out the tool data from the readable data carrier, and the identification device further configured to automatically and autonomously detect activation of an antenna of the at least one tool holder and/or packaging and to read out the readable data carrier of the at least one tool holder and/or packaging.

11. An identification method for automatically identifying a medical engineering tool via an identification system for automatic identification of a medical engineering tool, the identification system having at least one tool holder and/or packaging provided with a readable data carrier and which is configured to hold the medical engineering tool and having an identification device configured to read out tool data from the readable data carrier to identify the medical engineering tool, the tool, the at least one tool holder and/or the packaging configured in such a way that readability of the readable data carrier is automatically activated by removal of the medical engineering tool, the identification device being further configured to detect when readability of the readable data carrier is activated and automatically read out the tool data from the readable data carrier, the identification method comprising the following steps:

detecting activation of an antenna attached to the at least one tool holder and/or packaging by removing the medical engineering tool from the at least one tool holder and/or packaging;

reading out tool data of the readable data carrier of the at least one tool holder and/or packaging; and storing and/or transmitting the tool data.

12. The identification method according to claim 11, further comprising the step of comparing the medical engineering tool with a stored and set application and identifying whether the medical engineering tool is suitable for the application.

13. The identification method according to claim 11, further comprising at least one of:

updating additional data; and updating the tool data of the readable data carrier of the at least one tool holder and/or packaging.

\* \* \* \* \*